United States Patent [19]

Ward et al.

[11] 4,101,662
[45] Jul. 18, 1978

[54] METHOD FOR INHIBITING EMESIS AND COMPOSITIONS THEREFOR

[75] Inventors: John Wesley Ward; Charles Arthur Leonard, both of Richmond, Va.

[73] Assignee: A. H. Robins Company, Incorporated, Richmond, Va.

[21] Appl. No.: 356,975

[22] Filed: May 3, 1973

[51] Int. Cl.² .......................................... A61K 31/445
[52] U.S. Cl. .................................................. 424/267
[58] Field of Search ........................................ 424/267

[56] References Cited

U.S. PATENT DOCUMENTS

| 3,128,278 | 4/1964 | Craig et al. | 424/267 |
| 3,576,810 | 4/1971 | Duncan et al. | 424/267 |
| 3,852,455 | 12/1974 | Carr | 424/267 |

OTHER PUBLICATIONS

Martin et al., Remington Practice of Pharmacy, 12th Ed., pp. 1052-1059, (1976), Mack Pub. Co., Easton, Pa.

*Primary Examiner*—Frederick E. Waddell

[57] ABSTRACT

1,4-(3-)Disubstituted piperidines are disclosed which have useful antiemetic properties. The compounds have the general formula:

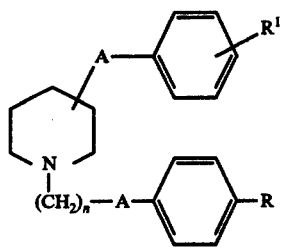

wherein R is halogen, $R^1$ is hydrogen and halogen, n is a positive integer from 2-4 and A is —C(O)— and —CHOH—. The pharmaceutically acceptable acid addition salts of the basic compounds are particularly useful as antiemetics.

8 Claims, No Drawings

METHOD FOR INHIBITING EMESIS AND COMPOSITIONS THEREFOR

The present invention relates to a method for inhibiting emesis and nausea associated therewith and to materials and compositions suitable therefor, and is more particularly concerned with the application for this purpose of certain 1,4-(3-)disubstituted piperidines.

The antiemetic agents of the invention are illustrated generally by the following structural formula:

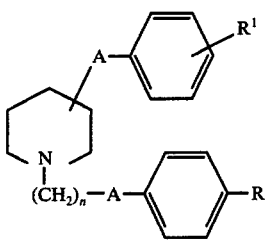

Formula I wherein;
R is halogen,
$R^1$ is selected from the group consisting of hydrogen and halogen,
n is a positive integer from 2–4 inclusive,
A is selected from the group consisting of —C(O)— and —CHOH—, and pharmaceutically acceptable acid addition salts thereof.

Certain of the 1,4-(3-)disubstituted piperidines which are used in the methods and compositions of the present invention are disclosed and methods for their preparation are given in Duncan and Helsley U.S. Pat. No. 3,576,810. The disclosure of said patent is hereby incorporated by reference as fully as though set forth herein. The methods disclosed therein are particularly applicable to the preparation of compounds of Formula I which are 4-(3-)benzoyl-1-[3-(p-halobenzoyl)propyl]-piperidines and 4-(3-)halobenzoyl-1-[3-(p-halobenzoyl)-propyl]-piperidines.

Compounds of Formula I wherein A is —CHOH— are prepared by (a) sodium borohydride reduction of a 1,3-dioxolane of Formula II according to the following reaction:

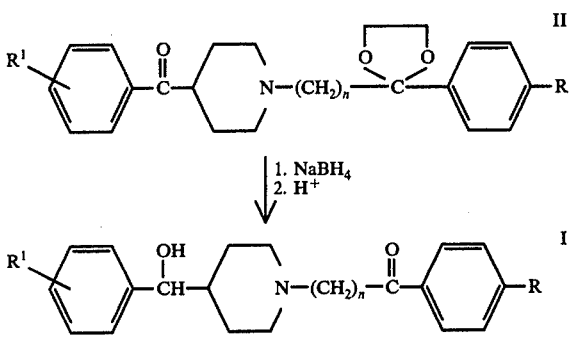

or by (b) sodium borohydride reduction of a diketone of Formula I according to the following reaction:

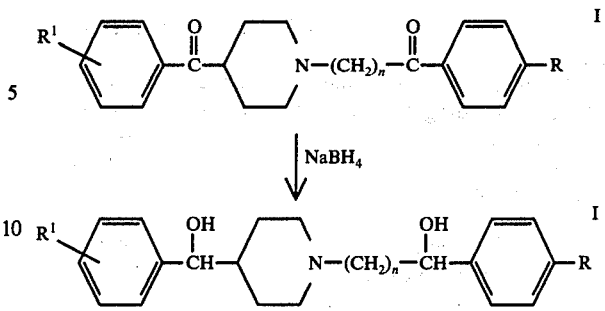

wherein R, $R^1$ and n are as defined above. The methods of preparation of the compounds of Formula I are more fully disclosed in the examples.

The compounds employed as active antiemetics are thus the free bases and pharmaceutically acceptable acid addition salts thereof of 1,4-(3-)disubstituted piperidines, as will more readily be seen from the foregoing Formula I. The acid addition salts include such usual nontoxic and pharmaceutically acceptable salts as the maleate, fumarate, ascorbate, hydrochloride and hydrobromide. The hydrochloride is especially preferred. The salts are readily formed by methods well known to the art by treatment of the free base with the appropriate salt forming substance, including, for example, maleic acid, fumaric acid, ascorbic acid, hydrochloric acid, hydrobromic acid, or similar salt forming substances.

The term halogen includes those halogens having an atomic weight less than 80. The preferred halogen is fluorine.

The present invention involves the discovery that certain 1,4-(3-)disubstituted piperidines and especially 4-(p-fluorobenzoyl)-1-[3-(p-fluorobenzoyl)propyl]-piperidine and its hydrochloride, are capable of suppressing emesis without concurrently inducing undesirable side effects. Because of the high degree of effectiveness and freedom from complicating side effects of these compounds, the administration thereof of the compositions in pharmaceutical dosage amounts is not only possible but clearly indicated. In the dosage amounts employed for antiemetic activity, the compositions of this invention have little or no side effects such as hypotension and extrapyramidal reactions.

It is, therefore, a primary object of the present invention to provide a method for inhibiting emesis by the administration of certain 1,4-(3-)disubstituted piperidines. It is another object of this invention to provide an antiemetic method, and compositions for the use therein, which is capable of effecting antiemetic results without concurrently inducing undesirable side effects. A further object is to provide antiemetic compositions containing novel active ingredients which may be administered in low concentrations in a suitable vehicle or carrier.

An additional object of the present invention is to provide compositions embodying certain 1,4-(3-)disubstituted piperidines for administration to inhibit emesis. An especial object is the provision of such a method and composition which employs as active antiemetic 4-(p-fluorobenzoyl)-1-[3-(p-fluorobenzoyl)propyl]piperidine hydrochloride (Example 1).

Additional objects and advantages of the present invention will be apparent to one skilled in this art, and still others will become apparent from the following description of the best mode of carrying out the present invention and examples thereof, and from the appended claims.

Of the number of compounds which may be employed according to the invention and embraced by Formula I, preferred compounds are the 4-(halobenzoyl)-1-[3-(p-halobenzoyl)propyl]piperidines and their acid addition salts, especially their hydrochlorides.

The method of inhibiting emesis in accord with the method of the present invention involves the administration of a compound of the foregoing Formula I, especially 4-(p-fluorobenzoyl)-1-[3-(p-fluorobenzoyl)propyl]piperidine in the form of its hydrochloride having the structural formula:

Formula II

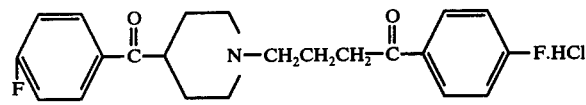

Description of this invention will therefore be made with especial emphasis on 4-(p-fluorobenzoyl)-1-[3-(p-fluorobenzoyl)propyl]piperidine hydrochloride, it being understood that the principles and practices involved are applicable to the other compounds of the formula first hereinabove set forth. The antiemetic activity of the compounds was determined by the following standard pharmacological tests.

The compounds were administered orally (PO) in gelatin capsules to dogs which had been shown to be sensitive to the emetic effect of apomorphine. The compounds were administered two hours prior to the subcutaneous administration of apomorphine hydrochloride (0.1 mg./kg.). The data are summarized in Table I.

TABLE I

| Example | Dose mg/kg PO | Percent Reduction in Frequency of Emesis |
|---|---|---|
| 1 | 2.0 | − 100 |
|   | 0.2 | − 30 |
| 2 | 2.0 | − 96 |
| 3 | 2.0 | − 100 |
| 4 | 2.0 | − 4 |

The compounds were administered intramuscularly (IM) to unanesthetized dogs in the caudal muscles (left hind leg) and thirty minutes later they received apomorphine hydrochloride (0.1 mg./kg. s.c.). The compounds were administered in micrograms (mcg.) at several dose levels and the percent reduction in frequency of emesis relative to controls determined. From the data the $ED_{50}$ in micrograms was determined. The data are summarized in Table II.

TABLE II

| Example | $ED_{50}$ and 95% Confidence Limits (mcg/kg) IM |
|---|---|
| 1 | 8.3 (3.1–22.3) |
| 2 | 60.0 (45–81) |
| 3 | 77.0 (21–288) |
| 4 | 1401.0 (796–2468)[a] |
| 9 | 132.0 (77–225) |
| 10 | 1000.0[b] |

[a](Estimated Values).
[b]Value obtained from a graphic estimate.

The compounds of Examples 1–4 were all water soluble. The compounds of Examples 9–10 were dissolved in a vehicle consisting of 80% polyethylene glycol 300 and 20% water.

EXAMPLE 1

4-(p-Fluorobenzoyl)-1-[3-(p-fluorobenzoyl)propyl]-piperidine Hydrochloride

A mixture of 13.9 g. (0.057 mole) of 4-(p-fluorobenzoyl)piperidine hydrochloride, 15.5 g. (0.063 mole) of 2-(p-fluorophenyl)-2-(ω-chloropropyl)-1,3-dioxolane, and 27.6 g. (0.2 mole) of potassium carbonate in 150 ml. of 1-butanol was refluxed 20 hours. The mixture was filtered, the filtrate concentrated, the oily residue dissolved in 50 ml. of an ether-methanol mixture and this solution stirred with 100 ml. of 3N HCl for one hour. The mixture was cooled, the layers separated, the aqueous layer basified and the basic mixture extracted with ether. The ethereal extracts were dried over anhydrous sodium sulfate, the mixture filtered and the filtrate treated with ethereal hydrogen chloride. The salt, which weighed 17.2 g. (74%), was recrystallized from an isopropanol-methanol mixture. The dried hydrochloride salt melted at 255°–257° C. The free base which was prepared by neutralization of a portion of the hydrochloride salt melted at 133°–135° C.

Analysis: Calculated for $C_{22}H_{24}ClF_2NO_2$: C,64.78; H,5.93; N,3.44. Found: C,64.77; H,6.02; N,3.34.

EXAMPLE 2

4-(p-Fluorobenzoyl)-1-[3-(p-chlorobenzoyl)propyl]-piperidine Hydrochloride

A mixture of 4-(p-fluorobenzoyl)piperidine hydrochloride (9.75 g.; 0.04 mole), 2-(p-chlorophenyl)-2-(ω-chloropropyl)-1,3-dioxolane (10.5 g.; 0.04 mole) and sodium bicarbonate (13.5 g.; 0.16 mole) and 150 ml. of n-butanol was refluxed for twenty hours. The hot mixture was filtered and the filter cake washed with benzene. The combined filtrates were concentrated at reduced pressure. The residual material was dissolved in a minimum amount of absolute ethanol, 6N hydrochloric acid was added and the mixture stirred for 0.5 hour. Water was added to the mixture and the solid hydrochloride salt was isolated by filtration. The salt was recrystallized from isopropanol-methanol to give 6.3 g. (41%) of the hydrochloride salt which melted at 250°–252° C.

Analysis: Calculated for $C_{22}H_{24}Cl_2FNO_2$: C,62.27; H,5.46; N,3.30. Found: C,62.54; H,5.72; N,3.29.

EXAMPLE 3

4-(p-Chlorobenzoyl)-1-[3-(p-fluorobenzoyl)propyl]-piperidine Hydrochloride

Ten grams (0.023 mole) of 2-(p-fluorophenyl)-2-{3-[4-(p-chlorobenzoyl)piperidinyl]propyl}-1,3-dioxolane was stirred in 100 ml. 6N hydrochloric acid and 100 ml. methanol with warming to affect solution for two hours and then allowed to cool. The product separated as the hydrochloride salt. Six grams of the salt was collected by filtration; m.p. 261°–266° C. (yield 61%). The salt was recrystallized from methanol-isopropanol to give 4.0 g. salt. Treatment of the filtrate with anhydrous ether precipitated out another 0.5 g. of the salt. The two fractions had identical melting points (264°–266° C.).

Analysis: Calculated for $C_{22}H_{24}Cl_2FNO_2$: C,62.27; H,5.70; N,3.30. Found: C,62.49; H,5.71; N,3.32.

The 2-(p-fluorophenyl)-2-{3-[4-(p-chlorobenzoyl)-piperidinyl]propyl}-1,3-dioxolane was prepared by reacting 10 g. (0.045 mole) of 4-(p-chlorobenzoyl)piperidine and 13.6 g. (0.0555 mole) of 2-(p-fluorophenyl)-2-

(ω-chloropropyl)-1,3-dioxolane in 125 ml. of refluxing n-butanol containing 8.4 g. (0.10 mole) of sodium bicarbonates for a period of 22 hours. The cooled mixture was filtered and concentrated at reduced pressure to give 21.3 g. (100% yield) of an oil which crystallized on trituration.

EXAMPLE 4

4-(p-chlorobenzoyl)-1-[3-(p-chlorobenzoyl)propyl]-piperidine Hydrochloride

A mixture of 4-(p-chlorobenzoyl)piperidine hydrochloride (10.5 g.; 0.04 mole), 2-(p-chlorophenyl)-2-(ω-chloropropyl)-1,3-dioxolane (10.5 g.; 0.04 mole) and sodium bicarbonate (13.5 g.; 0.16 mole) of n-butanol was refluxed for twenty hours. The hot mixture was filtered, the filtrate was concentrated at reduced pressure and the residual material was dissolved in a mixture of ethanol and 6N hydrochloric acid. The mixture was stirred 0.5 hour and hydrochloride salt which separated was collected by filtration. The salt was recrystallized from isopropanol-methanol (charcoal) to give 9.2 g. (57%) of the hydrochloride salt which melted at 253°–256° C.

Analysis: Calculated for $C_{22}H_{24}Cl_3NO_2$: C,59.94; H,5.26; N,3.18. Found: C,60.07; H,5.42; N,3.23.

EXAMPLE 5

4-Benzoyl-1-[3-(p-fluorobenzoyl)-propyl]-piperidine Hydrochloride

A stirred mixture of 7.0 g. (0.037 mole) of 4-benzoyl-piperidine, 9.8 g. (0.040 mole) of 2-phenyl-2-(ω-chloropropyl)-1,3-dioxolane, 20 g. of $K_2CO_3$ and 100 ml. of 1-butanol was refluxed 16 hours, cooled, filtered and the solvent evaporated at reduced pressure. The residual oil was stirred with 100 ml. of 3N HCl and 100 ml. of ethanol for one hour. The mixture was made basic with 50% NaOH and the oil which separated was extracted with benzene. The combined extracts were washed with water, dried over magnesium sulfate and the solvent evaporated. The residue was dissolved in isopropanol and treated with ethereal hydrogen chloride. The white crystalline product which formed was recrystallized from an isopropanol-ethanol mixture. The salt weighed 8.4 g. (59% yield) and melted at 230°–233° C.

Analysis: Calculated for $C_{22}H_{25}ClFNO_2$: C,67.77; H,6.46; N,3.59. Found: C,67.58; H,6.41; N,3.61.

EXAMPLE 6

3-Benzoyl-1-[3-(p-fluorobenzoyl)-propyl]piperidine Hydrochloride

A stirred mixture of 5.7 g. (0.030 mole) of 3-benzoyl-piperidine, 8.3 g. (0.034 mole) of 2-(p-fluorobenzoyl)-2-(ω-chloropropyl)-1,3-dioxolane, 14 g. of potassium carbonate and 100 ml. of 1-butanol was refluxed 16 hours, cooled, filtered and the solvent evaporated at reduced pressure. After the residual oil was stirred with 100 ml. of 3N HCl and 100 ml. of ethanol for one hour, the solution was made basic with 50% NaOH and the oil which separated was extracted with benzene. The combined extracts were washed with water, dried over magnesium sulfate and the solvent evaporated at reduced pressure. The residual oil was dissolved in isopropanol and treated with ethereal hydrogen chloride. The white crystalline salt which formed melted with decomposition at 206°–208° C. and weighed 5.1 g. (44% yield) after it was recrystallized again from isopropanol.

Analysis: Calculated for $C_{22}H_{25}NO_2ClF$: C,67.77; H,6.46; N,3.59. Found: C,67.96; H,6.40; N,3.65.

EXAMPLE 7

2-(p-Fluorophenyl)-2-{3-[4-(p-fluorobenzoyl)-piperidino]propyl}-1,3-dioxolane

A mixture of 24.4 g. (0.1 mole) of 4-(p-fluorobenzoyl)piperidine hydrochloride, 24.5 g. (0.1 mole) of 2-(p-fluorophenyl)-2-(ω-chloropropyl)-1,3-dioxolane, and 33.6 g. (0.4 mole) of sodium bicarbonate in 450 ml. of 1-butanol was refluxed for 17 hr. The mixture was filtered and the filtrate was concentrated under reduced pressure. The crude residue was dissolved in benzene and placed on a magnesium silicate column. Elution with a benzene-acetone gradient gave 16.0 g. (24%) of pure product which crystallized. Recrystallization from isooctane gave the pure product melting at 62°–64° C.

Analysis: Calculated for $C_{24}H_{27}F_2NO_3$: C,69.38; H,6.55; N,3.37. Found: C,69.51; H,6.55; N,3.16.

EXAMPLE 8

2-(p-Fluorophenyl)-2-{3-[4-(p-fluoro-α-hydroxybenzyl)piperidino]propyl}-1,3-dioxolane A mixture of 3.78 g. (0.1 mole) of sodium borohydride in 25 ml. of anhydrous ethanol was stirred at room temperature. A solution of 8.16 g. (0.02 mole) of 2-(p-fluorophenyl)-2-{3-[4-(p-fluorobenzoyl)piperidino]-propyl}-1,3-dioxolane in 10 ml. of anhydrous ethanol was slowly added dropwise so as to maintain a controlled evolution of gas. After the addition was complete the mixture was allowed to stir at room temperature for 16 hr. A large excess of water was added and the mixture was extracted several times with benzene. The benzene extracts were dried with anhydrous sodium sulfate and filtered. The filtrate was concentrated under reduced pressure and a glass-like residue was obtained. The residue was dissolved in benzene and placed on a magnesium silicate column. Using a benzene-acetone gradient solution, the product was obtained. Recrystallization of the solid product from methanol-isooctane gave 6.5 g. (78%) of white solid melting at 114°–116° C.

Analysis: Calculated for $C_{24}H_{29}F_2NO_3$: C,69.04; H,7.00; N,3.36. Found: C,69.07; H,7.08; N,3.33.

EXAMPLE 9

4-(p-Fluoro-α-hydroxybenzyl)-1-[3-(p-fluorobenzoyl)-propyl]piperidine

A solution of 3.0 g. (0.0072 mole) of 2-(p-fluorophenyl)-2-{3-[4-(p-fluoro-α-hydroxybenzyl)piperidino]-propyl}-1,3-dioxolane in 5 ml. of chloroform was stirred at room temperature with 25 ml. of 6N hydrochloric acid for 2 hr. The mixture was poured onto crushed ice and an excess of 50% sodium hydroxide solution was added. The free base of the ketone crystallized upon neutralization. The solid which was obtained was recrystallized from benzene-isooctane and gave 1 g. of white solid melting at 144°–146° C.

Analysis: Calculated for $C_{22}H_{25}F_2NO_2$: C,70.75; H,6.75; N,3.75. Found: C,71.07; H,6.87; N,3.53.

EXAMPLE 10

4-(p-Fluoro-α-hydroxybenzyl)-1-[3-(p-fluoro-α-hydroxy)propyl]piperidine

To a stirring suspension of 4.3 g. (0.0116 mole) of 4-(p-fluorobenzoyl)-1-[3-(p-fluorobenzoyl)propyl]- piperidine in 100 ml. of absolute ethanol at 50° C. was added in small portions, 1.9 g. (0.05 mole) of sodium borohydride. After all the sodium borohydride had been added, stirring was continued at 50° C. for one hour. About 20 ml. of 3N hydrochloric acid was slowly added dropwise to the mixture. The reaction mixture was eluted to about 400 ml. of water and made slightly basic with sodium hydroxide. The mixture was extracted with chloroform and the chloroform extracts were dried over anhydrous magnesium sulfate. The mixture was filtered and the filtrate was concentrated under reduced vacuum to get 4.8 g. of oil which crystallized upon trituration in isooctane. The crude product weighed 4.1 g. (94–95%) and melted at 115°–117° C. Recrystallization from isooctane-benzene gave 3.6 g. melting at 115°–117° C.

Analysis: Calculated for $C_{22}H_{27}F_2NO_2$: C,70.38; H,7.25; N,3.73. Found: C,70.42; H,7.35; N,3.74.

EXAMPLE 11

4-(p-Chloro-α-hydroxybenzyl)-1-[3-(p-fluorobenzoyl)-propyl]piperidine

Sodium borohydride (0.4 g., 0.01 mole) was added in small portions to a stirring solution of 2.2 g. (0.0052 mole) of 2-(p-fluorophenyl)-2-{3-[4-(p-chlorobenzoyl)-piperidino]propyl}-1,3-dioxolane in 20 ml. of absolute ethanol. The reaction mixture was stirred until gas evolution ceased and then dilute hydrochloric acid was added dropwise until an acidic solution was obtained. After stirring overnight the mixture was diluted with water and basified with dilute sodium hydroxide. The free base was extracted into chloroform, the chloroform solution was washed with water, dried over magnesium sulfate, filtered, and the filtrate concentrated under vacuum. The residual oil crystallized on trituration with isopropyl ether to give 1.2 g. (60%) of a light brown solid which melted at 143°–146° C. Recrystallization of the solid from benzene-isooctane gave 0.8 g. of a white powdery solid which melted at 146.5°–147° C.

Analysis: Calculated for $C_{22}H_{25}ClFNO_2$: C,67.77; H,6.46; N,3.59. Found: C,67.52; H,6.39; N,3.42.

Effective quantities of any of the foregoing pharmacologically active compounds may be administered internally to animals including humans in any one of various ways, for example, orally as in capsules or tablets, parenterally in the form of sterile solutions or suspensions, and in some cases intravenously in the form of sterile solutions. The drug may also be administered rectally in the form of suppositories or by inhalation means. The free basic amine compounds, while effective, are preferably formulated and administered in the form of their nontoxic acid addition salts for purposes of convenience of crystallization, increased solubility and the like. When the active compounds are used in veterinary practice, they can be given per se as an additive to the feed or to the drinking water.

Although very small quantities of the active materials of the present invention, even as low as 0.1 milligram, are effective when minor therapy is involved or in cases of administration to animals, including humans; having a relatively low body weight, unit dosages are usually one half, one or two milligrams and can be two to five milligrams, depending, of course, on the emergency of the situation. One milligram to two milligrams appears optimum per unit dose. The active agents may be combined with other pharmacologically active agents, or with buffers, antacids or the like, for administration. It is only necessary that the active ingredient constitute an effective amount, i.e., such that a suitable effective dosage will be obtained consistent with the dosage form employed. Obviously, several unit dosages may be administered at about the same time.

The pharmaceutical carriers which can be used in the novel compositions of the present invention can be solids and liquids. Solid carriers can include but are not limited to lactose, starch, magnesium, stearate, corn starch, dicalcium phosphate, gelatin and calcium stearate. Liquid carriers can include but are not limited to peanut oil, olive oil, sesame oil and water.

The formulations of the following example are representative for the pharmacologically active compounds of the invention.

Example formulations (1) Capsules — Capsules of 0.5 mg., 1.0 mg., 2.0 mg. and 5.0 mg. of active ingredient per capsule are prepared.

| Typical blend for encapsulation | Per capsule, mg. |
|---|---|
| Active ingredient, as salt | 0.5 |
| Lactose | 325.0 |
| Starch | 104.5 |
| Magnesium stearate | 5.0 |
| Total | 435.0 |

Additional capsule formulations preferably contain a higher dosage of active ingredient and are as follows:

| Ingredient | 1.0 mg. per capsule | 2.0 mg. per capsule | 5.0 mg. per capsule |
|---|---|---|---|
| Active ingredient, as salt | 1.0 | 2.0 | 5.0 |
| Lactose | 325.0 | 324.0 | 320.0 |
| Starch | 104.0 | 104.0 | 105.0 |
| Magnesium stearate | 5.0 | 5.0 | 5.0 |
| Total | 435.0 | 435.0 | 435.0 |

In each case, uniformly blend the active ingredient with lactose, starch, and magnesium stearate and encapsulate the blend.

(2) Tablets — A typical formulation for a tablet containing 0.5 mg. of active ingredient per tablet follows. The formulation may be used for other strengths of active ingredient by adjustment of weight of dicalcium phosphate.

|  | Per tablet, mg. |
|---|---|
| (1) Active ingredient, as salt | 0.5 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 1.0 |
| Total | 165.7 |

Uniformly blend 1, 2, 4 and 5. Prepare 3 as a 10 percent paste in water. Granulate the blend with starch paste and pass the wet mass through an eight mesh screen. The wet granulation is dried and sized through a twelve mesh screen. The dried granules are blended with the calcium stearate and pressed.

Additional tablet formulations contain 1.0 mg., 2.0 mg., and 5.0 mg. of active ingredient and are prepared as described above.

(3) Injectable — 0.05% sterile solution.

|  | mg. per cc. |
| --- | --- |
| Active ingredient, as salt | 0.5 |
| Preservative, e.g., chlorobutanol percent wt./ml | 0.0125 |
| Water for injection, q.s. | |

Prepare solution, clarify by filtration, fill into vials, seal, and autoclave.

(4) Suppositories

| Ingredient | Amt. gms. |
| --- | --- |
| Active ingredient | 0.10 |
| Carbowax polyethylene glycol 1000 | 75.00 |
| Carbowax polyethylene glycol 4000 | 25.00 |

A melt is made of the carbowax materials, the active ingredient is added to the melt which is thoroughly mixed and then is poured into molds of 1.0 gm. capacity and allowed to cool. Each suppository contains 1.0 mg. of active ingredient.

Various modifications and equivalents will be apparent to one skilled in the art and may be made in the compositions and methods of the present invention without departing from the spirit or scope thereof, and it is therefore to be understood that the invention is to be limited only by the scope of the appended claims.

What is claimed is:

1. A method of inhibiting emesis and nausea in an animal or human in need of said treatment which comprises internally administering to said animal or human from about one half milligram to about five milligrams of a compound selected from 1,4-(3-)-disubstituted piperidines of the formula:

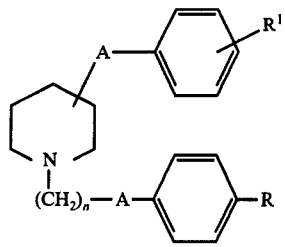

wherein;
R is halogen having an atomic weight less than 80,
$R^1$ is selected from the group consisting of hydrogen and halogen having an atomic weight less than 80,
n is a positive integer from 2–4 inclusive,
A is selected from the group consisting of —C(O)— and —CHOH—, and
pharmaceutically acceptable acid addition salts thereof.

2. The method of claim 1 wherein a 4-(p-halobenzoyl)-1-[3-(halobenzoyl)propyl]piperidine and an acid addition salt thereof is administered.

3. The method of claim 1 wherein 4-(p-fluorobenzoyl)-1-[3-(p-chlorobenzoyl)propyl]piperidine is administered.

4. The method of claim 1 wherein 4-(p-chlorobenzoyl)-1-[3-(p-chlorobenzoyl)propyl]piperidine is administered.

5. The method of claim 1 wherein 4-(p-fluoro-α-hydroxybenzyl)-1-[3-(p-fluorobenzoyl)propyl]piperidine is administered.

6. The method of claim 1 in which the administration is orally to human beings.

7. The method of claim 1 in which the administration is parenterally to human beings.

8. A method of inhibiting emesis and nausea in an animal or human in need of said treatment which comprises internally administering to said animal or human from about one-half milligram to about five milligrams of 4-(p-fluorobenzoyl)-1-[3-(p-fluorobenzoyl)propyl]piperidine hydrochloride.

* * * * *